(12) United States Patent
Van Es

(10) Patent No.: US 7,430,772 B2
(45) Date of Patent: Oct. 7, 2008

(54) DEVICE INCLUDING MOVEABLE SUPPORT FOR EXAMINING PERSONS

(75) Inventor: Arthur Robert Van Es, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 443 days.

(21) Appl. No.: 10/558,123

(22) PCT Filed: May 19, 2004

(86) PCT No.: PCT/IB2004/050742

§ 371 (c)(1),
(2), (4) Date: Nov. 23, 2005

(87) PCT Pub. No.: WO2004/105603

PCT Pub. Date: Dec. 9, 2004

(65) Prior Publication Data

US 2006/0242764 A1    Nov. 2, 2006

(51) Int. Cl.
*A61G 7/10* (2006.01)
(52) U.S. Cl. .............................. 5/601; 5/943; 378/209
(58) Field of Classification Search .................. 5/601, 5/600, 943; 600/415; 378/209, 208
See application file for complete search history.

(56) References Cited

U.S. PATENT DOCUMENTS

| 5,199,123 A | 4/1993 | Jacques et al. | 5/601 |
| 5,272,776 A | 12/1993 | Kitamura | 5/81.1 |
| 6,615,428 B1 * | 9/2003 | Pattee | 5/601 |

FOREIGN PATENT DOCUMENTS

| WO | WO 02/32310 A1 | 4/2002 |
| WO | WO 03/037182 A1 | 5/2003 |

* cited by examiner

Primary Examiner—Alexander Grosz

(57) ABSTRACT

A device for the examination of persons including a medical examination device (11) having an examination volume (12), a support (1) for a person to be examined, and a drive assembly (3) for displacing the support in a displacement direction in such a manner, that a person to be examined present on the support is displaced into and out of the examination volume. The drive assembly includes a gear-wheel (7), which is driven by a driving device (5, 8) and co-operates with a toothed rack (4) mounted to the support for displacing the toothed rack relative to the gear-wheel in the driven state of the gear-wheel. The drive assembly includes an auxiliary moving assembly (6, 9) for displacing the gear-wheel in its driven state in the displacement direction with a speed which is lower than the speed of support.

12 Claims, 5 Drawing Sheets

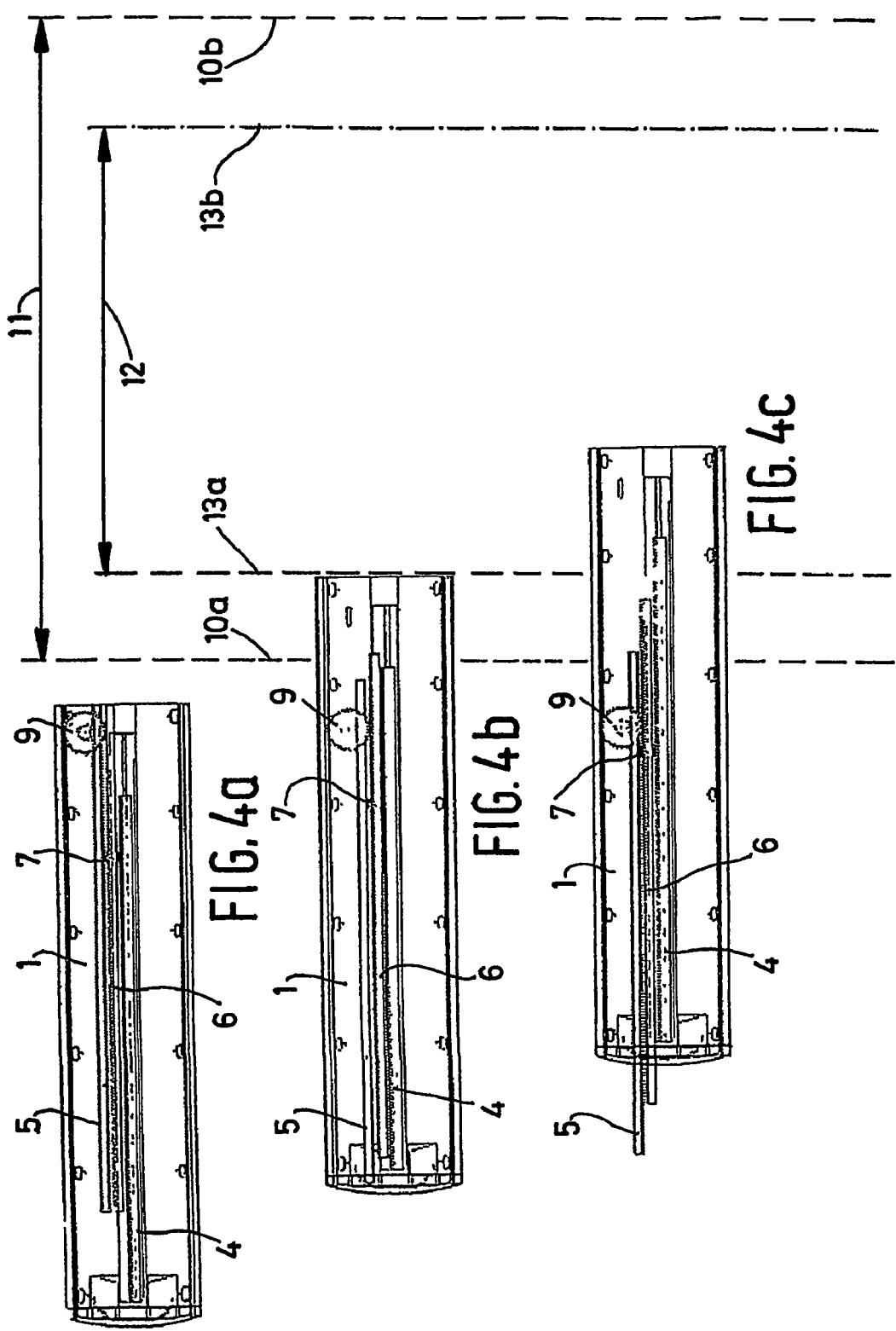

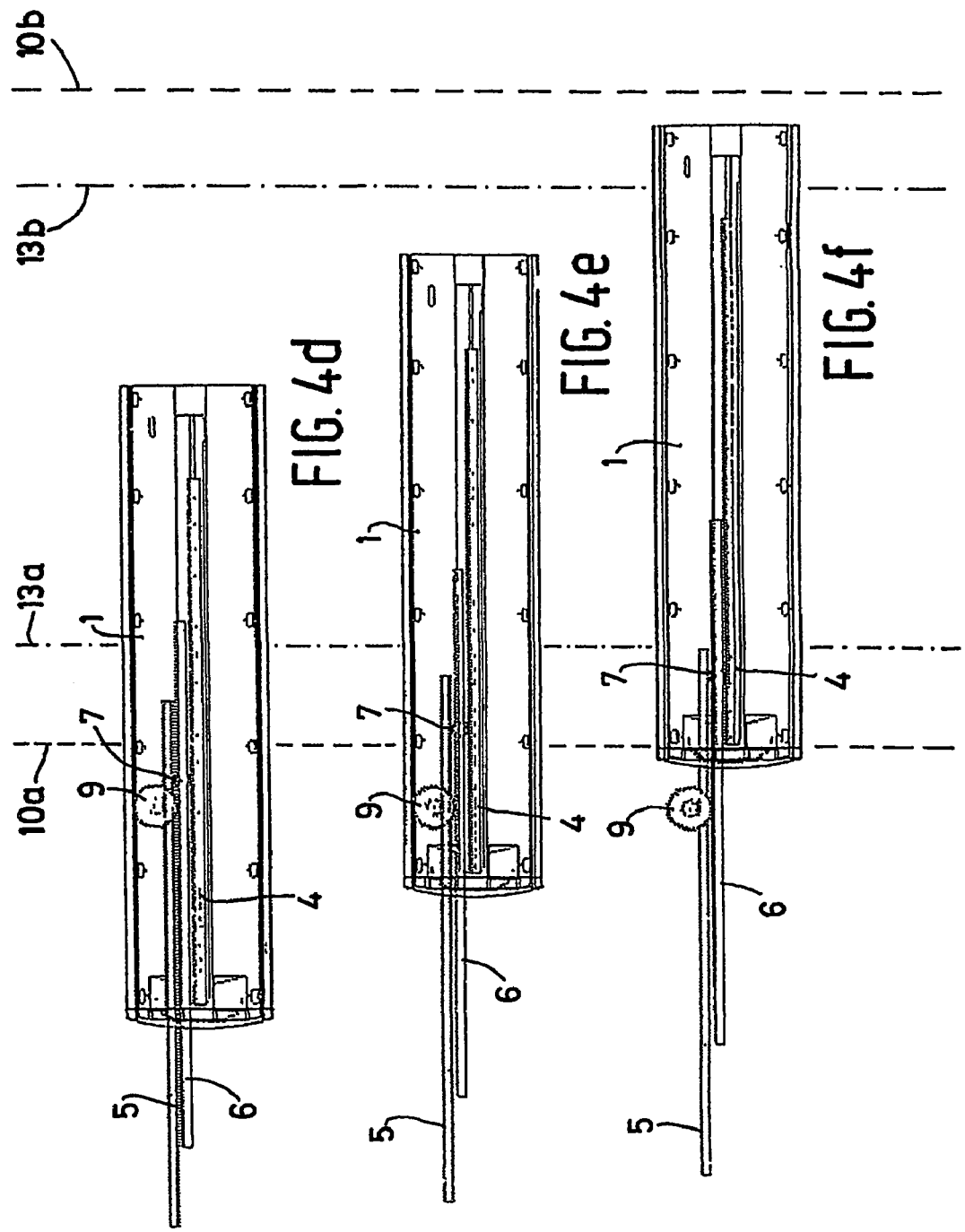

DEVICE INCLUDING MOVEABLE SUPPORT FOR EXAMINING PERSONS

The invention relates to a device for examining persons, comprising a medical examination device having an examination space, a support for a person to be examined, and means for moving the support in a direction of movement, in such a manner that a person to be examined who is present on said support is moved into and out of the examination space, said moving means comprising a gear wheel driven by driving means, which gear wheel, when driven, is in mesh with a toothed rack connected to the support for moving the toothed rack relative to the gear-wheel.

Within the framework of the invention, a medical examination device as referred to above is in particular an MRI device, by means of which images can be obtained of internal parts of the body of a person who is present in the examination space of the MRI device. When medical examination devices of this kind are used, a person to be examined usually positions himself on a support outside the examination space, after which the support is moved in the direction of the examination space, as a result of which the person to be examined enters the examination space in order for the examination in question to be carried out.

A device as referred to in the introduction is described in U.S. Pat. No. 5,272,776. The device is a closed-type MRI scanner, which is characterized by an annular housing, in the center of which the examination space is present. The MRI device described therein comprises a bed system, which is supported by roller elements inside the MRI scanner. The bed system can be moved from a position outside the examination space to a position in which the bed system is largely present within the examination space, possibly together with a person to be examined who is present thereon. In order to effect this movement, the bed system is provided with a toothed rack extending in the direction of movement, which is in mesh with a gear wheel which is rotated, via a transmission, by a drive unit that forms part of the MRI device. The gear wheel is present at a location outside the axial length of the MRI device, and one end of the bed system cannot pass said gear wheel during movement. This implies that one end of the bed system will be positioned outside the axial length of the MRI scanner on the outer side of the gear wheel at all times, even when the bed system is moved into the examination space as far as possible. At said end, a leg, to the lower end of which a wheel is mounted, which wheel can roll on the supporting surface that also supports the MRI device, supports the bed system. In the situation in which the bed system has been moved out of the examination space as far as possible, it remains necessary for the bed system to extend partially within the axial length of the MRI device, in connection with the necessary support by the roller elements that are present at locations within the axial length of the MRI device.

The prior art MRI device as briefly described above has various drawbacks. In the first place, the construction of the bed system makes it necessary for the bed system to have a comparatively large length in order to be able to move a person to be examined sufficiently far into and out of the examination space. In addition, an important drawback is the fact that, in use, a person to be examined must position himself on the bed system, or needs to be positioned thereon by nursing staff, with the MRI device. This takes time, during which time the medical examination device, in this case the MRI device, is not utilized efficiently, and it will be apparent that it is preferable for economic and capacity considerations to be able to examine as many persons as possible by means of the medical examination device.

It is an object of the invention to provide, whether or not in preferred embodiments thereof, a solution or at least a significant improvement with regard to the aforesaid drawbacks.

In order to achieve this object, a device for examining persons according to the invention is characterized in that the moving means comprise auxiliary moving means for moving the gear wheel in the direction of movement when the gear wheel is being driven, at a speed that is lower than the speed at which the support is being moved. This characterizing aspect makes it possible in principle to extend the stroke of the support, even to the extent that it becomes possible for the support to be moved over a distance greater than the length of the support itself, or at least for one end of the support to pass the spatial position of the gear wheel in an extreme position during its movement, which is not possible with the device according to the prior art. This in turn makes it possible to use a comparatively short support having a length not greater than required for supporting a person to be examined.

Preferably, the auxiliary moving means comprise a driven auxiliary gear wheel, which meshes with an auxiliary toothed rack for moving said auxiliary toothed rack with respect to said auxiliary gear wheel when said auxiliary gear wheel is being driven, with the gear wheel being journalled with respect to said auxiliary toothed rack. Thus a constructionally simple and practically embodiment for moving the gear wheel according to the invention is obtained.

A suitable, because of its simplicity, construction for rotating the gear wheel is obtained in a further embodiment, in which the moving means comprise further auxiliary moving means for moving a further auxiliary toothed rack in the direction of movement at a speed which is lower than the speed of the auxiliary toothed rack and the gear wheel that is journalled therein, with said further auxiliary toothed rack being in mesh with said gear wheel. The gear wheel functions as a transmission element between said further auxiliary toothed rack and the toothed rack that is connected to the support. A further gear wheel may be provided between the gear wheel and said further auxiliary toothed rack, in which said gear wheel and said further gear wheel are jointly rotatable about a common axis, for example, or in which said gear wheel and said further gear wheel have different diameters, for example, or in which said gear wheel and said further gear wheel are in mesh with each other, for example.

Preferably, said further auxiliary moving means comprise a further auxiliary gear wheel which meshes with said further auxiliary toothed rack. Thus the movement of said further auxiliary toothed rack can be effected in a simple manner.

When said auxiliary gear wheel and said further auxiliary gear wheel as described above are used in combination with preferred embodiments of the invention, it is furthermore preferable for said auxiliary gear wheel and said further auxiliary gear wheel to be rotatably journalled about a common axis of rotation. In this way said auxiliary gear wheel and said further auxiliary gear wheel can be driven at the same angular speed in a simple manner.

According to a very special preferred embodiment, a freely wheeled chassis supports the support when the support is not present in the examination space. This provides a major advantage in that a person to be examined can position himself on the support in a room other than the room in which the medical examination device is disposed, after which the person to be examined is wheeled to the medical examination device, whereupon the medical examination can be carried out within the shortest possible time and the person in question can be wheeled to another room again. An important additional advantage is the fact that it is also possible in that case to use a number of freely wheeled chassis, each provided with a support, so that a next person can be examined in the medical examination device immediately after a first person has been examined by means of the medical examination device, with the first person still being present on a support.

In this connection it is preferable for the chassis to comprise the moving means and/or the driving means. The supply of power to the driving means may take place by means of a battery, for example, which also forms part of the chassis, or by simply connecting the driving means to the electricity mains by means of a power plug, for example.

Within the framework of the preferred embodiments of a device according to the invention as described above, in which a freely wheeled chassis is used, the invention also relates to a combination of the chassis and the support for use in such a preferred embodiment of a device according to the invention the advantages of such a combination have already been explained above within the framework of the respective preferred embodiments of the device according to the invention.

The present invention will be explained in more detail hereinafter by means of a description of a preferred embodiment of a device according to the invention, in which reference is made to the following figures.

FIGS. 4*a*-4*f* are bottom plan views of successive positions during the movement of a support from a position completely outside the examination space of a medical examination device to a position at least partially inside the examination space of the medical examination device.

Figure 1:
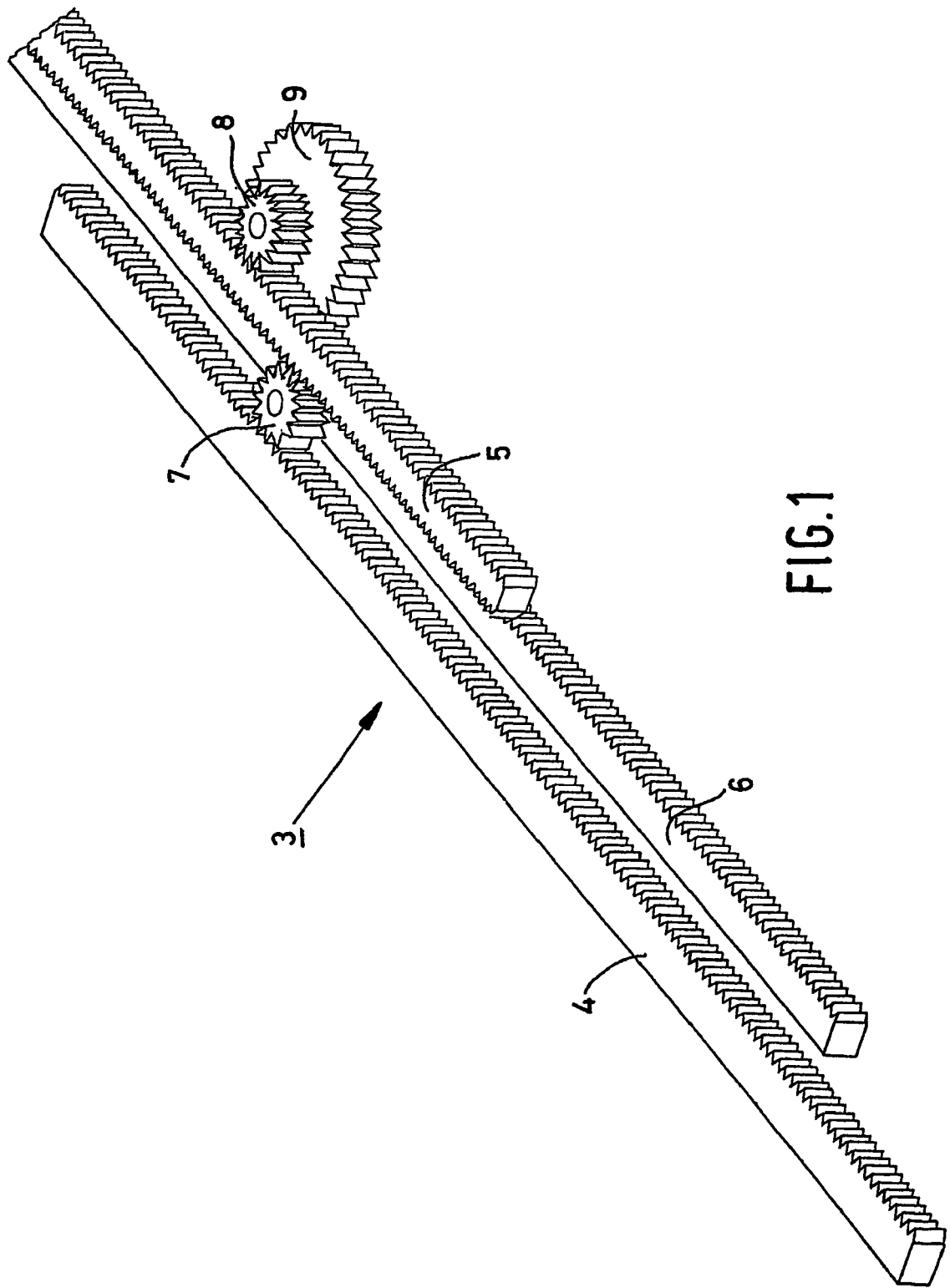
FIG. 1 is a perspective top plan view of gear wheels and toothed racks as used in the preferred embodiment of a device according to the invention, approximately in the position as shown in FIG. 4*d*.
Figure 2:
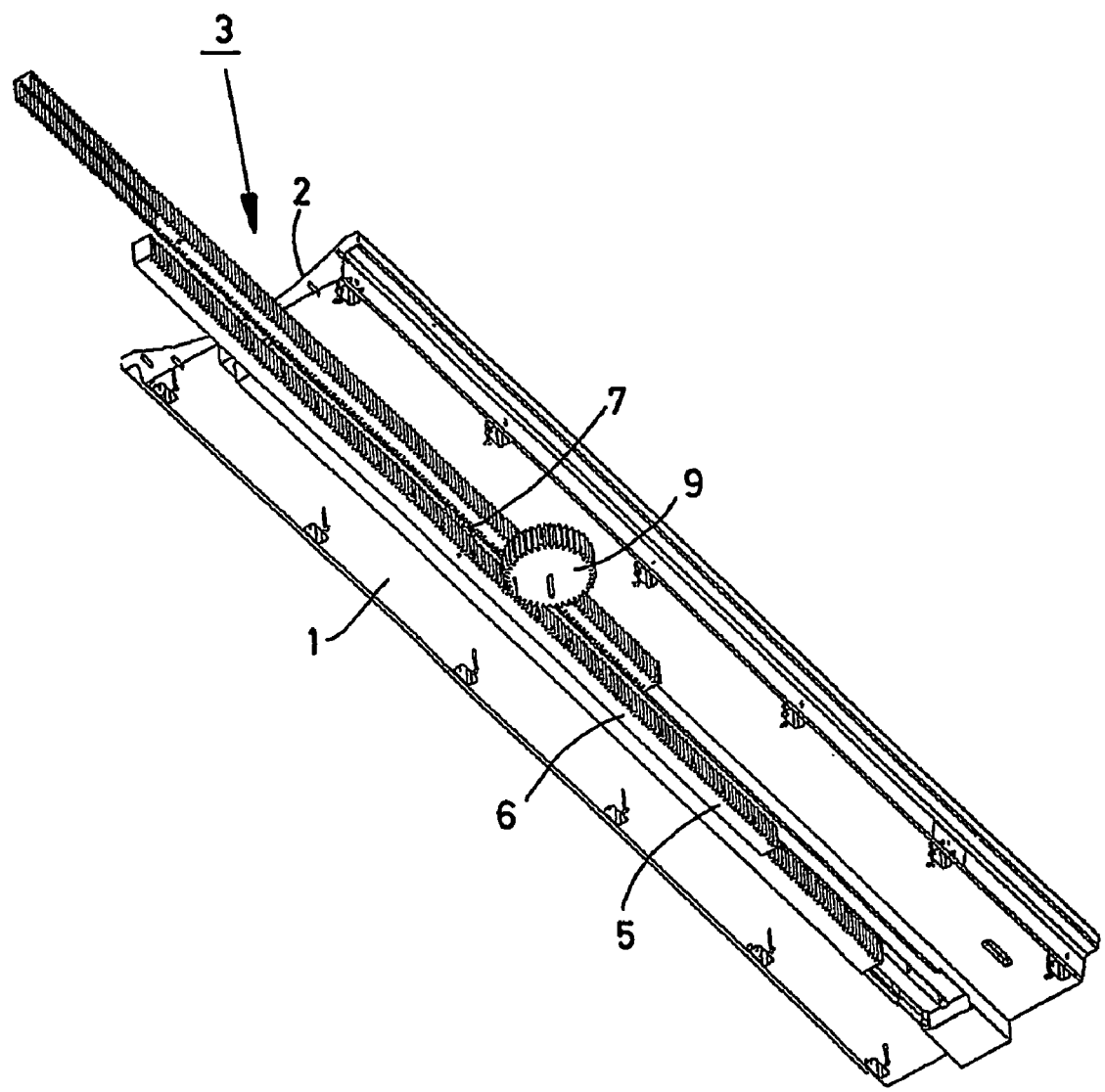
FIG. 2 is a perspective bottom plan view of the gear wheels and the toothed racks of FIG. 1 and a support for a patient to be examined, approximately in the position as shown in FIG. 4*c*.
Figure 3:
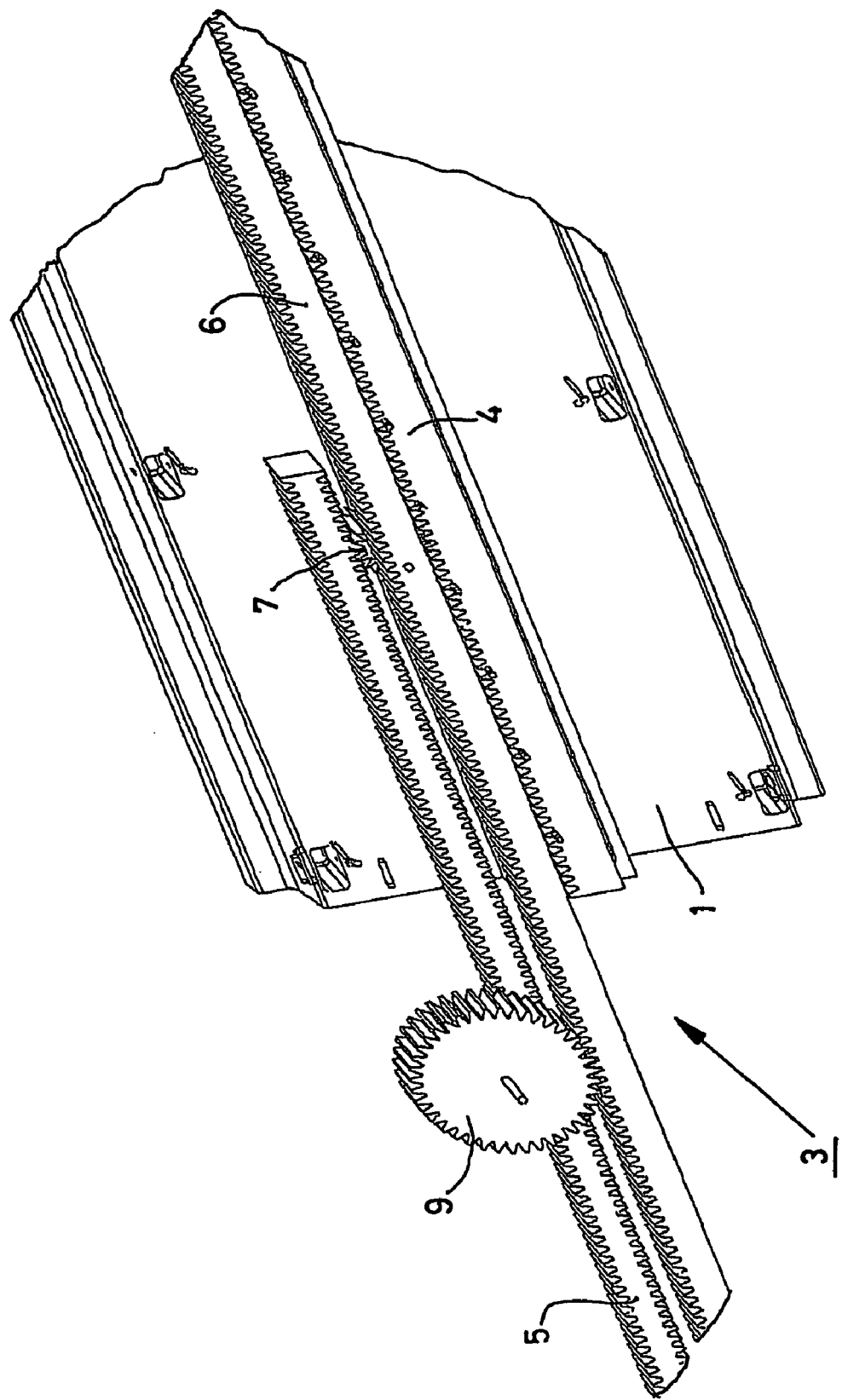
FIG. 3 is a more detailed, perspective bottom plan view approximately in the position as shown in FIG. 4*f*.

FIGS. 2 and 3 are different perspective bottom plan views of a support 1. The slightly concave upper side 2 of the support 1 is intended for supporting a person in a recumbent posture. Present at the bottom side of the support 1 is a multiple rack and pinion mechanism 3, which is shown in perspective top plan view, without the support 1, in FIG. 1.

The multiple rack and pinion mechanism 3 comprises three toothed racks 4, 5, 6 extending parallel to each other as well as three gear wheels 7, 8 and 9. The gear wheel 7 is rotatably mounted to the rack 6 at the upper side thereof. The toothed rack 6 is positioned between the toothed rack 4 and the toothed rack 5, seen in top plan view, albeit at a lower position. The toothed racks 4 and 5 are positioned at the same vertical level, namely the vertical level of the gear wheel 7, as a result of which the gear wheel 7 can mesh both with the toothed rack 4 and with the toothed rack 5. The toothed rack 4 is rigidly connected to the support 1, so that the support 1 and the toothed rack 4 are only capable of joint movement. The toothed rack 5 is provided with teeth on two opposite sides thereof. The gear wheel 8 meshes with the toothed rack 5 on the side opposite the side where the gear wheel 7 is present. A gear wheel 9 having a larger diameter than the gear wheel 8 is positioned concentrically with the gear wheel 8, which gear wheel 9 extends partially below the toothed rack 5 so as to mesh with the teeth of the toothed rack 6. The gear wheels 8 and 9 are rigidly connected to a drive shaft (not shown) for rotating the gear wheels 8 and 9 at the same angular speed. Because of the different diameters of the gear wheels 8 and 9, common rotation of the gear wheels 8 and 9 will result in the toothed racks 5 and 6 moving in their longitudinal direction at different speeds. In this case, the speed of movement of the toothed rack 6 and thus of the gear wheel 7 will be greater than that of the toothed rack 5, as a result of which the gear wheel 7 will roll along the toothed rack 5. Since the gear wheel 7 meshes with the toothed rack 4, the rotation of the gear wheel 7 that is thus generated will in turn cause the toothed rack 4 to move in its longitudinal direction with respect to the gear wheel 7, at a speed of movement greater than that of the toothed rack 6 (and logically greater than that of the toothed rack 5).

The multiple rack and pinion mechanism 3 as described above can be used to great advantage for moving the support 1 into and out of an examination space of a medical examination device, such as an MRI scanner. All this will be explained in more detail with reference to FIGS. 4*a*-4*f*. The dashed lines 10*a*, 10*b* indicate the ends of a closed-type MRI scanner 11 as known to those skilled in the art. The ends of the examination space 12 inside the MRI scanner 11, in which a (part of a) person to be examined must be present in order to undergo the examination by means of the MRI scanner 11, are indicated by the chain-dotted lines 13*a*, 13*b*.

The support 1 (with a person to be examined present thereon) is initially (FIG. 4*a*) positioned beside the MRI scanner 11, with the support 1 itself being supported by a mobile chassis (not shown). The drive shaft, via which the gear wheels 8 and 9 are driven, is mounted in bearings in said chassis, whilst the chassis also comprises the required electric driving motor for driving said drive shaft. The supply of electric power to said driving motor takes place by connecting the driving motor to the electricity mains by means of a power plug. Alternatively it is possible to use a chassis-mounted battery. It is important to establish that the gear wheels 8 and 9 continue to take up the same spatial position during movement of the support 1 with respect to the MRI scanner 11 as shown in FIGS. 4*a*-4*f*, as will be explained in more detail hereinafter.

When the driving motor is energized, the gear wheels 8 and 9 will start to rotate at the same speed, as a result of which the toothed racks 5 and 6 will move in the direction of the examination space 12 of the MRI scanner 11. The speed of the toothed rack 6 is higher than that of the toothed rack 5, as a result of which the toothed rack 4, too, will move in the direction of the examination space 12 together with the support 1, and that at a speed that is even greater than that of the toothed rack 6. FIGS. 4*a*-4*f* show successive positions in which the support 1 is being moved further and further into the examination space 12. It will be apparent that guides are present inside the MRI scanner 11 for guiding and supporting the support 1. Such guides are also known from U.S. Pat. No. 5,272,776, in which they are indicated at 9. It will also be apparent to those skilled in the art that guiding arrangements are present that function to prevent pivoting of the toothed racks 4, 5, 6 upon movement thereof in their respective longitudinal directions.

From FIG. 4*b*, the support 1 is shown to be entering the examination space 12, whilst the support 1 fully occupies said examination space 12 in the position that is shown in FIG. 4*f*, with the ends of the support 1 largely being present within the MRI scanner. FIG. 4*f* furthermore shows that the support 1 has completely passed the gear wheel 9, and thus also the starting position of the gear wheel 7 in FIG. 4*a*, and that the support 1 has traveled a distance greater than its own length in comparison with the position that is shown in FIG. 4*a*.

The support 1 is retracted in a simple manner again by reversing the direction of rotation of the gear wheels 8, 9, with the support successively moving through the positions that are shown in FIGS. 4f-4a. Once the situation as shown in FIG. 4a has been reached, the support 1 and the MRI scanner 11 are no longer connected in any way, so that the support 1 can be driven off on the mobile chassis.

All kinds of the variants of the preferred embodiment as described above are possible within the scope of the present invention. Thus, a fourth toothed rack may be provided, for example, which meshes with a gear wheel which is rotatably mounted on the toothed rack 4, which fourth toothed rack can move even faster (and further) than the toothed rack 4. Furthermore, the invention may comprise embodiments in which the construction of the auxiliary moving means for moving the gear wheel 7 in the direction of movement does not comprise the toothed rack 5 and the gear wheel 8. The gear wheel 7 may be mounted in bearings in a carrier, for example, which can be moved by means of an alternative moving arrangement, in which the driving means for driving the gear wheel 7 are likewise mounted on the carrier and comprise a separate motor, for example.

The invention claimed is:

1. A device for examining persons, comprising:
   a medical examination device having an examination space,
   a support for a person to be examined, and
   means for moving the support in a direction of movement, in such a manner that a person to be examined who is present on said support is moved into and out of the examination space, said moving means comprising:
     a driven gear wheel, the gear wheel meshing with a first toothed rack connected to the support for moving the first toothed rack relative to the gear-wheel when the gear wheel is being driven,
     a first auxiliary moving means for moving the gear wheel in the direction of movement when the gear wheel is being driven, at a first speed which is lower than the speed at which the support is being moved and
     a second auxiliary moving means including an element which moves in the direction of movement at a speed slower than the first speed.

2. The device as claimed in claim 1, wherein the first auxiliary moving means comprise a driven auxiliary gear wheel, which meshes with an auxiliary toothed rack for moving said auxiliary toothed rack with respect to said auxiliary gear wheel when said auxiliary gear wheel is being driven, with the gear wheel being journalled with respect to said auxiliary toothed rack.

3. The device as claimed in claim 1, wherein the support is supported by a freely wheeled chassis when the support is not present in the examination space.

4. The device as claimed in claim 3, wherein the chassis comprises the moving means.

5. The device as claimed in claim 3, wherein the chassis comprises the driving means.

6. A combination of said chassis and said support for use in a device as claimed in claim 3.

7. A device for examining persons, comprising:
   a medical examination device having an examination space,
   a support for a person to be examined, and
   a drive assembly for moving the support in a direction of movement, in such a manner that a person to be examined who is present on said support is moved into and out of the examination space said drive assembly comprising:
     a gear wheel driven by driving device, the gear wheel meshing with a toothed rack connected to the support for moving the toothed rack relative to the gear-wheel when the gear wheel is being driven,
     the drive assembly including an auxiliary moving assembly for moving the gear wheel in the direction of movement when the gear wheel is being driven, at a speed which is lower than a speed at which the support is being moved, the auxiliary moving assembly including:
       a driven auxiliary gear wheel, which meshes with a first auxiliary toothed rack for moving said auxiliary toothed rack with respect to said auxiliary gear wheel when said auxiliary gear wheel is being driven, with the gear wheel being journalled with respect to said auxiliary toothed rack,
       a further auxiliary toothed rack moving in the direction of movement at a speed which is lower than the speed of the first auxiliary toothed rack and the gear wheel that is journalled therein, with said further auxiliary toothed rack being in mesh with said gear wheel.

8. The device as claimed in claim 7, wherein said further auxiliary moving means comprise a further auxiliary gear wheel which meshes with said further auxiliary toothed rack.

9. The device as claimed in claim 8, wherein said auxiliary gear wheel and said further auxiliary gear wheel are rotatably journalled about a common axis of rotation.

10. A drive mechanism for moving a support in a direction of movement, in such a manner that a person to be examined who is present on said support is moved in a direction of movement into and out of a examination space of a medical examination device, said mechanism comprising:
    a first gear wheel driven by a motor, the first gear wheel meshing with a first toothed rack connected to the support such that the first toothed rack and the support move in the direction of movement relative to the first gear wheel when the first gear wheel is being driven,
    a second toothed rack, the first gear wheel being mounted to the second toothed rack such that the second toothed rack and the first gear wheel move in the direct of movement when the first gear wheel is being driven,
    a third toothed rack element,
    second and third gear wheels with a common axis of rotation, a larger of the second and third gear wheels meshing with the second toothed rack element and a smaller of the second and third gears meshing with the third toothed rack element.

11. A patient table comprising:
    a support for carrying a patient;
    a chassis on which the support is carried; and
    the drive device as claimed in claim 10 for moving the support relative to the chassis.

12. A patient examination system comprising:
    a diagnostic examination device which defines an examination space;
    a base connected to the diagnostic examination device carrying a support for carrying a patient in the direction of movement into and out of the examination space; and
    the drive mechanism as claimed in claim 10 for moving the support into and out of the examination space.

* * * * *